United States Patent [19]

Hall et al.

[11] 4,159,341

[45] Jun. 26, 1979

[54] ANTI-ALLERGIC BIS-PHENYLENE COMPOSITIONS AND METHODS OF USING SAME

[75] Inventors: Charles M. Hall; John B. Wright, both of Kalamazoo, Mich.

[73] Assignee: The Upjohn Company, Kalamazoo, Mich.

[21] Appl. No.: 839,864

[22] Filed: Oct. 6, 1977

Related U.S. Application Data

[62] Division of Ser. No. 645,024, Dec. 29, 1975, Pat. No. 4,061,791.

[51] Int. Cl.² .................. A61K 31/24; A61K 31/275
[52] U.S. Cl. ............................. 424/309; 260/465 B; 260/465 D; 424/304; 424/316; 424/317; 424/319; 560/13; 560/34; 562/427
[58] Field of Search .............. 424/304, 309, 316, 317, 424/319; 260/518 A, 518 R, 516; 560/34, 12, 13, 35, 64; 562/427

[56] References Cited

U.S. PATENT DOCUMENTS

| 3,639,249 | 2/1972 | Luethi et al. | 252/300 |
| 3,966,965 | 6/1976 | Sellstedt et al. | 424/309 |

*Primary Examiner*—Leonard Schenkman
*Attorney, Agent, or Firm*—Martin B. Barancik

[57] ABSTRACT

A method of treating mammals for allergy and anaphylactic reactions of a reagin or non-reagin mediated nature which comprises administering prophylactically to said mammal an anti-allergy or anaphylactic reaction effective amount of a compound of the formula

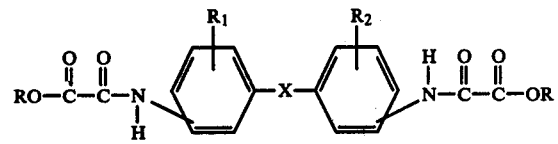

Novel compositions are also claimed.

9 Claims, No Drawings

ANTI-ALLERGIC BIS-PHENYLENE COMPOSITIONS AND METHODS OF USING SAME

CROSS REFERENCE TO RELATED APPLICATIONS

This application is a division of copending U.S. application Ser. No. 645,024, filed Dec. 29, 1975, now U.S. Pat. No. 4,061,791.

BRIEF SUMMARY OF THE INVENTION

It has now been discovered that compounds of Formula I are useful in the prophylactic treatment of sensitized humans and animals for allergy and anaphylactic reactions of a reagin or non-reagin mediated nature. The compounds are formulated with pharmaceutical carriers for oral, parenteral, inhalation or rectal means of administration. Certain compounds are novel.

DETAILED DESCRIPTION OF THE INVENTION

In accordance with the invention, there is provided a method of prophylactically treating mammals for allergy and anaphylactic reactions of a reagin or non-reagin mediated nature which comprises administering to said mammal an anti-allergy or anaphylactic reaction effective amount of a compound of the formula

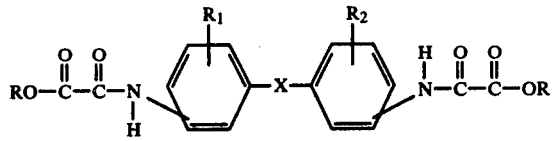

wherein

R is selected from the group consisting of hydrogen, a physiological acceptable metal or amine cation, alkyl of one to six carbon atoms, and

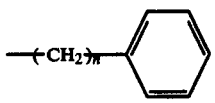

wherein n is 0, 1 or 2;

$R_1$ and $R_2$ are the same or different and are selected from the group consisting of hydrogen, halogen, nitro, cyano and

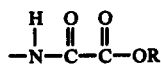

with the proviso that when one or both of $R_1$ and $R_2$ are

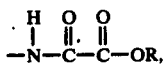

the two

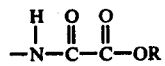

groups on a phenylene ring are not ortho to each other;

X is selected from the group consisting of $-(CH_2)_{\overline{m}}$ wherein m is zero, 1, 2, or 3, O, S, SO, $SO_2$,

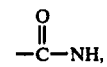

$O(CH_2)_pO$, $HN(CH_2)_pNH$ wherein p is an integer of 1 to 3, $OCH_2CHOHCH_2O$, and

wherein $R_4$ is selected from the group consisting of hydrogen and alkyl of one to three carbon atoms, inclusive, in association with a pharmaceutical carrier.

A sub-group of compounds, hereafter referred to as Group A, which can be employed in the above disclosed method are the compounds of Formula I wherein R is selected from the group consisting of hydrogen, a physiologically acceptable metal or amine cation and alkyl of one to six carbon atoms, inclusive;

$R_1$ and $R_2$ are the same or different and are selected from the group consisting of hydrogen, halogen, nitro, cyano, and

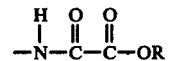

with the same proviso as above; and

X is selected from the group consisting of $-(CH_2)_{\overline{m}}$ wherein m is zero, 1, 2, or 3, O, $SO_2$,

and

wherein $R_4$ is selected from the group consisting of hydrogen and alkyl of one to three carbon atoms, inclusive.

A further sub-group of compounds of Group A, herein referred to as Group B, which can be employed in the above disclosed method are those compounds wherein R is selected from the group consisting of hydrogen, a physiologically acceptable metal or amine cation and alkyl of one to three carbon atoms, inclusive;

$R_1$ and $R_2$ are the same or different and are selected from the group consisting of hydrogen, halogen, cyano and nitro; and X is selected from the group consisting of $-(CH_2)_{\overline{m}}$ wherein m is 0 or 1, O, $SO_2$, and

Another aspect of the invention is a pharmaceutical composition having as the sole active ingredient an anti-allergy or anti-anaphylactic reaction effective amount of a compound of Formula I in association with a pharmaceutical carrier. Compounds of Groups A and B are also included within this concept.

A further aspect of the invention is a pharmaceutical composition having as the sole active ingredient an anti-allergy or anaphylactic effective amount of a compound of Formula I in association with a pharmaceutical carrier which is strongly resistant to degradation from untraviolet light. Compounds of Groups A and B are also included within this concept.

A still further aspect of the invention is an inhalation pharmaceutical composition comprising an anti-allergy or anaphylactic effective amount of a compound of Formula I in association with a pharmaceutical carrier. Compounds of Groups A and B are also included within this concept. Preferred compounds are those wherein R is selected from the group consisting of hydrogen and a physiologically acceptable metal or amine cation.

Another aspect of the invention is a pharmaceutical composition which comprises an anti-allergy or anaphylactic effective amount of a compound of Formula I wherein R is selected from the group consisting of hydrogen and a physiologically acceptable metal or amine cation in association with a pharmaceutical carrier. Compounds of Group A and B are also included within this concept.

Another aspect of the invention is a compound of Formula I wherein R is selected from the group consisting of hydrogen and a physiologically acceptable metal or amine cation. Compounds of Groups A and B are also included within this concept.

A further aspect of this invention is a compound of Formula I wherein $R_1$ and $R_2$ are selected from the group consisting of cyano, nitro, and

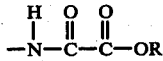

with the above proviso. Compounds of Groups A and B are within the concept.

Another aspect of the invention is a compound of Formula I wherein the

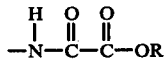

group is not at the 4 and/or the 4' position. Compounds of Groups A and B are within the concept.

A still further aspect of the invention is a compound of Formula I wherein X is selected from the group consisting of SO,

$O(CH_2)_pO$, $HN(CH_2)_pNH$ wherein p is 1, 2, or 3, and $OCH_2CHOHCH_2O$.

As employed throughout the specification and claims, the phrase "alkyl of one to six carbon atoms, inclusive" includes methyl, ethyl, propyl, butyl, pentyl, hexyl, and isomers thereof. Illustrative examples of isomers are isopropyl, tert-butyl, neopentyl, and 2,3-dimethylbutyl. The term "halogen" includes fluoro, chloro, bromo, and iodo. The phrase "a physiologically acceptable metal or amine cation" is that metal or amine which is accepted in an essentially non-toxic manner by a mammal. Illustrative examples of such metals are the alkali metals, e.g., lithium, sodium, and potassium, and the alkaline earth metals, e.g., magnesium and calcium. Other metals, e.g., aluminum, zinc, and iron are also within the scope of this invention. Illustrative of the amines are those derived from primary, secondary, or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about eighteen carbon atoms as well as heterocyclic amines, e.g. piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,5-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tertamylphenyl)diethanolamine, galactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium, and the like.

A pharmaceutical carrier strongly resistant to degradation from ultra-violet light includes materials employed in pharmaceutical compositions which do not readily decompose upon exposure to ultra-violet light over a reasonable period of time and may be used in pharmaceutical compositions without any protective devices such as amber colored containers. Examples of pharmaceutical carriers which are strongly resistant to ultra-violet degradation are water, alcohol, lactose, starch, talc and any other pharmaceutical carrier commonly used for bulking characteristics. A pharmaceutical carrier which may be considered as sensitive to ultra-violet degradation is a carrier which contains dyes and/or flavors.

The compounds are prepared by well known methods, for example, those included in U.S. Pat. No. 3,639,249, U.S. Pat. No. 3,852,324 and Ser. Number 382,762 issued as U.S. Pat. No. 3,993,679. Starting materials are readily available in the art or prepared from literature references.

Illustrative species of the inventions within this disclosure are set forth in the following table. The abbreviation "ox" employed in the Table refers to the ethyl oxamate group.

TABLE I

| X | $R_1$ | $R_2$ | $-N-C-COC_2H_5$ |
|---|---|---|---|
| $CH_2$ | H | H | 4,4' |
| $(CH_2)_2$ | H | 4'-CN | 4,3' |
| $(CH_2)_3$ | 6-$NO_2$ | H | 2,2' |
| $(CH_2)_0$ | 2-ox | H | 4,2' |
| $CH_2$ | 2-Cl | H | 3,3' |
| $(CH_2)_2$ | 2-Br | 4'-CN | 3,6' |

TABLE I-continued $$H_5C_2OC\overset{O}{\overset{\|}{-}}C\overset{O}{\overset{\|}{-}}N\overset{H}{\overset{|}{-}}\underset{R_1}{\overset{4}{\underset{5}{\bigcirc}}\overset{3}{\underset{6}{}}\overset{2}{\underset{1}{}}}-X-\underset{R_2}{\overset{2'}{\underset{6'}{\bigcirc}}\overset{3'}{\underset{5'}{}}\overset{4'}{\underset{}{}}}N\overset{H}{\overset{|}{-}}C\overset{O}{\overset{\|}{-}}COC_2H_5$$

$$-\overset{H}{\overset{|}{N}}-\overset{O}{\overset{\|}{C}}-\overset{O}{\overset{\|}{C}}OC_2H_5$$

| X | R₁ | R₂ |  |
|---|---|---|---|
| (CH₂)₃ | H | H | 4,4' |
| (CH₂)₁₀ | 2-NO₂ | 2'-ox | 4,4' |
| S | H | 2'-F | 6,6' |
| S | 3-NO₂ | H | 2,3' |
| S | 2-CN | 2'-CN | 4,4' |
| S | 3-I | 5'-NO₂ | 2,6' |
| S | 2-Cl | 2'-Cl | 3,4' |
| S | 2-ox | 4'-CN | 4,3' |
| S | 3-CN | 4'-NO₂ | 4,6' |
| S | 5-ox | 3'-ox | 3,5' |
| SO | H | H | 4,4' |
| SO | 2-Cl | 4'-NO₂ | 3,3' |
| SO | 3-CN | 3'-CN | 2,2' |
| SO | 3-F | 6'-ox | 4,2' |
| SO₂ | 2-NO₂ | 5'-H | 4,3' |
| SO₂ | H | H | 4,4' |
| SO₂ | 4-CN | 2'-ox | 2,6' |
| SO₂ | 6-Br | 4'-CN | 3,5' |
| CONH | H | H | 4,4' |
| CONH | H | 5'-CN | 3,3' |
| CONH | 4-NO₂ | 3'-Cl | 2,2' |
| CONH | 2-F | 6'-ox | 4,2' |
| CONH | 6-ox | 5'-ox | 4,3' |
| CONH | 2-Cl | 5-CN | 4,4' |
| OCH₂O | H | 4'-CN | 2,6' |
| O(CH₂)₂O | 2-NO₂ | 3'-ox | 3,5' |
| O(CH₂)₃O | 2-Cl | 2'-Cl | 4,4' |
| HN(CH₂)NH | 2-CN | 4'-CN | 3,3' |
| HN(CH₂)₂NH | 4-NO₂ | 5'-Br | 2,2' |
| HN(CH₂)₃NH | H | 3'-F | 2,4' |
| OCH₂CHOHCH₂O | 2-NO₂ | H | 4,4' |
| OCH₂CHOHCH₂O | H | 4'-CN | 2,3' |
| NH | 2-ox | 4-Cl | 4,2' |
| NCH₃ | 3-NO₂ | 5-CN | 4,4' |
| NC₂H₅ | 4-Br | 4'-Br | 3,3' |
| NC₃H₇ | H | 5'-ox | 2,3' |

TABLE II

The compounds of Table I are transesterified to esters wherein R is methyl, propyl, butyl, pentyl, hexyl, isomers thereof, phenyl, benzyl and phenethyl by standard methods.

TABLE III

The esters of Table II are hydrolyzed to the acid form of the compound by contact with base, followed by acid.

TABLE IV

The acids of Table III are converted to metal or amine salts, particularly tris(hydroxymethyl)amino methane salts by standard reaction conditions.

Following are illustrative preparations of compounds of the invention which are formulated into pharmaceutical compositions and used in the methods of this invention. All temperatures are in degrees centigrade.

EXAMPLE 1

N,N'-(Methylene-p-diphenylene)dioxamic Acid

Diethyl N,N'-(methylene-p-diphenylene)dioximate (1.0 g.) is heated at reflux for two hours in 1.0 N aqueous sodium hydroxide. The cooled reaction mixture is filtered and the insoluble disodium salt stirred at room temperature in 1.0 N hydrochloric acid. The desired diacid is collected by filtration and washed with acetone (4.68 g., mp >320°, sinters ca. 250°). The ir spectrum is consistent with the assigned structure.

EXAMPLE 2

3'-[m-(1-Carboxyformamido)benzamido]-oxanilic acid hydrate a. 3,3'-Dinitrobenzanilide To a stirred solution of 13.81 g. (0.1 mole) of m-nitroaniline in 100 ml. of dry ethyl acetate is added 11.13 g. (0.11 mole) of triethylamine. To the solution is added a solution of 18.56 g. (0.1 mole) of m-nitrobenzoylchloride in 100 ml of ethyl acetate. The mixture is refluxed for 6.5 hours. The reaction mixture is allowed to stand at room temperature overnight. The precipitate is removed by filtration. The filtrate is evaporated to dryness in vacuo. The residue is recrystallized from absolute ethanol. There is obtained 5.79 g. of yellow needles that melt at 188°–189°.

The original precipitate is washed several times with water. The wet precipitate is boiled with 1 liter of ethanol. The insoluble material is removed by filtration. There is obtained 8.45 g. of yellow needles that melt at 188°–189°. The filtrate, when refrigerated, produces another crop of product. There is obtained 10.85 g. of yellow needles that melt at 188°–189°. The total yield is 87% (25.09 g.).

b. 3,3'-Diaminobenzanilide

A solution of 14.3 g. of 3,3'-dinitrobenzanilide in 150 ml. of dioxane is hydrogenated at three atmospheres of hydrogen using 1 g. of 10% palladium-on-charcoal catalyst. The catalyst is removed by filtration and the filtrate evaporated to dryness. The residue is recrystallized from ethanol. There is obtained 8.72 g. of material melting at 123°–4°.

Analysis Calc'd for: $C_{13}H_{13}N_3O$ C, 68.70; H, 5.77; N, 18.49. Found: C, 68.49; H, 5.77; N, 18.71.

c. 3'-[m-(1-carboxyformamido)benzamido]-oxanilic Acid, Diethyl ester

To a solution of 7.72 g. (0.028 mole) of 3,3'-diaminobenzanilide in 25 ml. of dimethylformamide and 150 ml. of ethyl acetate is added 6.72 g. (0.067 mole) of triethylamine. The solution is cooled to 0° in an ice bath. To the solution is added 9.14 gm. (0.067 mole) of ethyl oxalyl chloride. The reaction mixture is stirred at room temperature for eight hours.

The precipitate is removed by filtration. The precipitate is stirred in 600 ml. of water. The insoluble material is removed by filtration. The solid material is recrystallized from 95% ethanol. There is obtained 10.8 g. (90%) of colorless needles that melt at 218°–220°.

Analysis Calc'd for: $C_{21}H_{21}N_3O_7$; C, 59.01; H, 4.95; N, 9.83. Found: C, 58.58; H, 4.90; N, 9.85.

d. 3'[m-(1-Carboxyformamido)benzamido]-oxanilic acid hydrate

A suspension of 9.80 gm. (0.023 mole) of 3'-[m-(1-carboxyformamide)benzamido]-oxanilic acid, diethyl ester, and 100 ml. of methylene chloride is placed in a separatory funnel. To the mixture is added 50 ml. of 1 N sodium hydroxide and the funnel shaken. The sodium salt forms and 600 ml. of water is added. The phases are shaken and separated. The aqueous phase is acidified with dilute hydrochloric acid. The precipitate is removed by filtration. There is obtained 8.50 gm. (99%) of a yellow solid that melts at 205° (dec.).

Analysis Calc'd for: $C_{17}H_{13}N_3O_7 \cdot H_2O$; C, 52.44; H, 3.88; N, 10.79. Found: C, 52.04; H, 3.73; N, 11.06.

EXAMPLE 3

4'-[m-(1-carboxyformamido)benzamido]-3'-cyanooxanilic acid a. 2'-Cyano-3,4'-dinitrobenzanilide

A solution of 8.16 gm. (0.05 mole) of 2-amino-5-nitrobenzonitrile and 9.28 gm. (0.05 mole) of m-nitro benzoyl chloride in 50 ml. of dry pyridine is refluxed for three hours. The pyridine is removed by distillation in vacuo and the solid residue triturated with water. There is obtained 15.3 gm. (95%) of a yellow solid that melts at 203°–205°. Recrystallization from aqueous ethanol (2:1) gives material melting at 205°–206°.

Analysis Calc'd for: $C_{14}H_8N_4O_5$; C, 52.17; H, 2.98; N, 17.38. Found: C, 53.68; H, 2.70; N, 17.83.

b. 4'-[m-(1-Carboxyformamido)benzamido]-3'-cyanooxanilic acid, diethyl ester To a solution of 14.4 gm. (0.05 mole) of 2'-cyano-3,4'-dinitrobenzanilide in 300 ml. of dioxane is added 1 gm. of 10% palladium on carbon. The reaction mixture is hydrogenated at three atmospheres of pressure of hydrogen.

The catalyst is removed by filtration. The filtrate is evaporated to dryness in vacuo and the solid recrystallized from ethanol-water. There is obtained 7.71 g. of material that melts at 180°–181°.

The compound is dissolved in 25 ml. of dimethylformamide and 100 ml. of ethyl acetate. To the solution is added 7.29 gm. (0.072 mole) of triethylamine. The solution is cooled to 0° in an ice bath and to the stirred solution is added 9.83 g. (0.072 mole) of ethyl oxalyl chloride.

The mixture is stirred in an ice bath for one hour. The reaction mixture is allowed to stand at room temperature overnight.

The precipitate is removed by filtration. The filtrate is evaporated to dryness in vacuo. The residue is recrystallized from 95% ethanol. There is obtained 3.33 gm. of yellow needles that melt at 159°–160°. The original precipitate is stirred in 250 ml. of water. The insoluble material is removed by filtration and the solid material recrystallized from 95% ethanol. There is obtained 7.00 gm. of yellow needles that melt at 159°–160°. The total yield was, thus, 10.33 gm. (70%).

Analysis Calc'd for: $C_{22}H_{20}N_4O_7$; C, 58.40; H, 4.46; N, 12.39. C, 56.87; H, 4.46; N, 12.29.

c. 4'-[m-(1-Carboxyformamido)benzamido]-3'-cyano oxanilic acid

A solution of 6.78 gm. (0.015 mole) of 4'-[m-(1-carboxyformamido)benzamido]-3'-cyano oxanilic acid, diethyl ester in 36 ml. of 1 N sodium hydroxide is diluted with 100 ml. of water. The solution is stirred for twenty minutes at room temperature and filtered. The filtrate is acidified with dilute hydrochloric acid. The precipitate is removed by filtration and the precipitate recrystallized from 95% ethanol. There is obtained 1.85 gm. of yellow material that melts at 245° (dec.).

Analysis Calc'd for: $C_{18}H_{12}N_4O_7$; C, 54.55; H, 3.05; N, 14.14. Found: C, 53.32; H, 3.04; N, 13.95.

EXAMPLE 4

4'-[p-(1-Carboxyformamido)benzamido]-3'-cyanooxanilic acid dihydrate a. 2-Cyano-4,4'-dinitrobenzanilide

To a stirred solution of 16.3 gm. (0.1 mole) of 5-nitroanthranilonitrile in 100 ml. of dry pyridine is added 18.56 gm. (0.1 mole) of p-nitrobenzoyl chloride. The reaction mixture is refluxed for three hours. The pyridine is distilled in vacuo. The oily residue is poured into 600 ml. of water and is distilled in vacuo. The oily residue is poured into 600 ml. of water and the precipitate removed by filtration. The precipitate is boiled with 1500 ml. of ethanol. The insoluble material is removed by filtration. There is obtained 21.57 gm. of yellow solid that melts at 195°–196°.

Analysis Calc'd for: $C_{14}H_8N_4O_5$; C, 53.85; N, 2.58; N, 17.94. Found: C, 53.86; H, 2.75; N, 17.89.

b. 4,4'-Diamino-2'-cyanobenzanilide

To a solution of 20.5 gm. (0.065 mole) of 2-cyano-4,4'-dinitrobenzanilide in 300 ml. of dioxane is added 1 gm. of 10% palladium on carbon. The mixture is hydrogenated at three atmospheres of hydrogen. The catalyst is removed by filtration and washed well with hot dioxane. The filtrate is evaporated to dryness in vacuo. There is obtained 11.6 gm. of material that melts at 240°–244°. Recrystallization from dioxane-ether gives material melting at 242°–244°.

Analysis Calc'd for: $C_{14}H_{12}N_4O$; C, 66.57; H, 4.79; N, 22.18. Found: C, 66.20; H, 5.05; N, 21.54.

c. 4'-[p-(1-Carboxyformamido)benzamido]-3'-cyanooxanilic Acid, diethyl ester To a stirred solution of 10.6 gm. (0.042 mole) of 2-cyano-4,4'-diaminobenzanilide in 25 ml. of dimethylformamide and 150 ml. of ethyl acetate is added 10.12 gm. (0.1 mole) of triethylamine. The solution is cooled to 0° in an ice bath. To the cold solution is added 13.65 g. (0.1 mole) of ethyl oxalyl chloride. The reaction mixture is stirred in an ice bath for one hour. The mixture is allowed to stand overnight.

The precipitate is removed by filtration and recrystallized from 95% ethanol. There is obtained 11.70 gm. of yellow needles that melt at 274°–275°. The original filtrate is evaporated to dryness in vacuo. The residue is recrystallized from 95% ethanol. There is obtained 1.63 gm. additional material.

Analysis Calc'd for: $C_{22}H_{20}N_4O_7$; C, 58.40; H, 4.46; N, 12.39. Found: C, 58.33; H, 4.59; N, 12.40.

d. 4'-[p-(1-Carboxyformamido)benzamido]-3'-cyanooxanilic acid dihydrate

A solution of 6.78 gm. (0.015 mole) of 4'-[p-(1-carboxyformamido)benzamido]-3'-cyano-oxanilic acid, diethyl ester in 36 ml. of 1 N sodium hydroxide is diluted with 200 ml. of water. The solution is stirred at room temperature for twenty minutes and then acidified with dilute hydrochloric acid. The precipitate is removed by filtration. There is obtained 5.90 gm. of a yellow solid that melts at >300°.

Analysis Calc'd for: $C_{18}H_{12}N_4O \cdot 2H_2O$; C, 51.92; H, 3.87; N, 13.45. Found: C, 51.47; H, 3.32; N, 13.42.

EXAMPLE 5

N,N'-[5-[[m-carboxyformamido)phenyl]-carbamoyl]-m-phenylene]dioxamic acid a. 3,3'-5-Trinitrobenzanilide

To a stirred solution of 13.81 gm. of m-nitroaniline in 100 ml. of dry ethyl acetate and 11.13 gm. of triethylamine is added 23.06 gm. of 3,5-dinitrobenzoyl chloride. The reaction mixture is heated under reflux for one hour and allowed to stand overnight.

The precipitate is removed by filtration and the filtrate evaporated to dryness. The residue is combined with the precipitate, the total solid stirred with 500 ml. of water and then boiled with 500 ml. of ethanol. The insoluble material is removed by filtration. There is obtained 20.2 gm. of material melting at 205°–6°.

Analysis Calc'd for: $C_{13}H_8N_4O_7$; C, 46.99; H, 2.43; N, 16.87. Found: C, 47.27; H, 2.55; N, 16.65.

b. 3,3',5-Triaminobenzanilide

A solution of 13.29 gm. (0.04 mole) of 3,3',5-trinitrobenzanilide in 150 ml. of dioxane is hydrogenated at three atmospheres of hydrogen using 1 gm. of 10% palladium-on-charcoal catalyst. The catalyst is removed by filtration, the filtrate evaporated to dryness under reduced pressure, and the residue dried by distilling 200 ml. of benzene from the reaction mixture.

c. N,N'-[5-[[m-(Carboxyformamido)phenyl]-carbamoyl]-m-phenylene]dioxamic acid, triethyl ester To a solution of 9.69 gm. of 3,3',5-triaminobenzanilide and 14.57 gm. of triethylamine in a mixture of 25 ml. of dry dimethylformamide and 150 ml. of dry ethyl acetate, cooled to 5°, is added 19.66 gm. of ethyl oxalyl chloride. The mixture is allowed to stand overnight. The precipitate is removed by filtration, stirred with water and refiltered. The precipitate is recrystallized from ethanol. There is obtained 10.0 gm. of material melting at 196°–8°.

Analysis Calc'd for: $C_{25}H_{26}N_4O_{10}$; C, 55.35; H, 4.67; N, 10.45. Found: C, 54.98; H, 4.67; N, 10.45.

d. N,N'-[5-[[m-carboxyformamido)phenyl]-carbamoyl]-m-phenylene]dioxamic acid A solution of 5.42 gm. (0.01 mole) of N,N'-[5-[[m-carboxyformamido)phenyl]-carbamoyl]-m-phenylene]dioxamic acid, triethyl ester in 50 ml. of 1 N sodium hydroxide solution and 200 ml. of water is stirred for twenty minutes. The solution is acidified and the resulting gelatinous precipitate removed by filtration, washed with water and dried in the air. There is obtained 4.51 gm. of material melting at 258° (dec.).

EXAMPLE 6

N,N'-[Sulfonylbis-(6-fluoro-m-phenylene)]-dioxamic acid a. 3,3'-Diamino-4,4'-difluorodiphenylsulfone

To a solution of 177 gm. of stannous chloride dihydrate in 400 ml. of concentrated hydrochloric acid is added 40.2 gm. of 4-fluoro-3-nitrophenylsulfone. The mixture is stirred and warmed to 50° and then allowed to stand at room temperature for three hours.

The reaction mixture is cooled and made strongly basic with a NaOH solution. The precipitate is filtered and the solid washed thoroughly with ethyl acetate. The extracts are dried over anhydrous MgSO$_4$ and the solvent removed. There is obtained 13.50 gm. of material melting at 154°–7°. Recrystallization from ethanol-water raises the melting point to 158°–9°.

Analysis Calc'd for: $C_{12}H_{10}F_2N_2SO_2$; C, 50.07; H, 3.54; F, 13.37; N, 9.85; S, 11.28. Found: C, 50.69; H, 3.56; F, 12.89; N, 10.08; S, 11.70.

b. Diethyl N,N'-[Sulfonylbis-(6-fluoro-m-phenylene]dioxamate

To a solution of 9.90 gm. (0.03 mole) of 3,3'-diamino-4,4'-difluorodiphenylsulfone in 100 ml. of dry ethyl acetate and 7.30 gm. (0.072 mole) of triethylamine cooled to 0° in an ice bath is added slowly 9.83 gm. (0.072 mole) of ethyl oxalyl chloride. The mixture is allowed to stand overnight at room temperature.

The precipitate is removed by filtration and the filtrate evaporated to dryness. The residue is recrystallized from ethanol. There is obtained 14.2 gm. of yellow needles melting at 137°–8°.

Analysis Calc'd for: $C_{20}H_{18}F_2N_2O_8S$; C, 49.58; H, 3.74; F, 7.84, N, 5.78; S, 6.62. Found: C, 49.72; H, 4.02; F, 8.05; N, 5.78; S, 6.61.

c. N,N'-[Sulfonylbis-(6-fluoro-m-phenylene)]-dioxamic acid

A solution of 4.84 gm. (0.01 mole) of diethyl N,N'-[Sulfonylbis-(6-fluoro-m-phenylene)]dioxamate in 130 ml. 0.23 N NaOH solution is stirred for twenty minutes and then acidified with dilute HCl. The yellow precipitate is removed by filtration. There is obtained 4.30 gm. of material melting at 214° (dec.). A sample is recrystallized for analysis from water.

Analysis Calc'd for: $C_{16}H_{10}F_2N_2SO_8$; C, 44.86; H, 2.35; F, 8.87; N, 6.54; S, 7.48. Found: (Calc'd for 1.47% water) C, 44.24; H, 2.41; F, 9.37; N, 6.23; S, 7.55.

EXAMPLE 7

N,N'-4,4'-Biphenylenedioxamic Acid a. Diethyl N,N'-4,4'-biphenylenedioxamate

A mixture of benzidine (18.4 gm., 0.1 mole) and diethyl oxalate (50 ml.) is heated at reflux for 2.5 hours. The cooled reaction mixture is diluted with ether (200 ml.) and the solid product collected by filtration (32.5 g., mp 215°–225°).

Analysis Calc'd for: $C_{20}H_{20}N_2O_3$; C, 62.49; H, 5.24; N, 7.29. Found: C, 62.82; H, 5.12; N, 7.33.

uv (EtOH) λmax (ε): 220 sh (14,400), 314 (30,000)mμ.

ir (Nujol): NH 3350, 3280; C=O 1725, 1695; C=C/amide II 1615, 1590, 1520, 1505 cm$^{-1}$ b. N,N'-4,4'-Biphenylenedioxamic Acid

Diethyl N,N'-4,4'-biphenylenedioxamate (10.0 gm.) is heated at reflux in 1.0 N aqueous sodium hydroxide (200 ml.) for two hours. The insoluble sodium salt is collected by filtration, and then heated at 80°–90° for 0.5 hours in 1.0 N hydrochloric acid. The desired diacid is collected (8.8 gm., mp >320°). The ir spectrum is consistent with the assigned structure.

EXAMPLE 8

N,N'-(Oxydi-p-phenylene)dioxamic Acid a. Diethyl N,N'-(oxydi-p-phenylene)dioxamate

A mixture of 4,4'-diaminodiphenylether (20.0 gm.) and diethyl oxalate (100 ml.) is refluxed for two hours. A small amount of solid is removed by filtration and the solvent removed under reduced pressure to leave an oil which crystallizes in methanol. Recrystallization from methanol and treatment with decolorizing charcoal gives an off-white solid (25.07 gm., mp 135°-140°). Thin layer chromatography (silica gel, chloroform) indicates the presence of two impurities. Chromatography on silica gel (methylene chloride) gives a sample of the desired compound (mp 150°-158°).

Analysis Calc'd for: $C_{20}H_{20}N_2O_7$; C, 59.99; H, 5.04; N, 7.00. Found: C, 60.12; H, 5.19; N, 6.91.

uv (EtOH) λmax (ε): 221 sh (13,350), 287 (21,150), 296 (20,400)mµ.

ir (Nujol): NH 3280; C=O 1730, 1690; C-C/amide II 1600, 1545, 1505cm$^{-1}$.

b. N,N'-(Oxydi-p-phenylene)dioxamic Acid

Diethyl N,N'-(oxydi-p-phenylene)dioxamate (2.0 gm.) is stirred at room temperature for three hours in 1.0 N sodium hydroxide (50 ml.). The solid is collected by filtration and dissolved in water. The pH is adjusted to pH=3 with concentrated hydrochloric acid and the desired product collected by filtration (1.6 gm., mp >320°).

The ir spectrum is consistent with the assigned structure.

EXAMPLE 9

Diethyl N,N'-(methylenedi-p-phenylene)-dioxamate

A mixture of 4,4'-diaminodiphenylmethane (19.8 gm., 0.10 mole) and diethyl oxalate is refluxed two and one-half hours. The solid product is filtered from the reaction mixture to leave an off-white solid. The solid is recrystallized once from acetone and once from methanol to give a white solid (14.4 gm., mp 130°-137°).

Analysis Calc'd for: $C_{21}H_{22}N_2O_6$; C, 63.31; H, 5.57; N, 7.03. Found: C, 63.56; H, 5.53; N, 7.01.

uv (EtOH) λmax (ε): 278 (20,650) mµ.

ir (Nujol): NH 3360, 3340; C=O 1730, 1705; C=C/amide II 1595, 1535, 1510 C-O/C-N/other 1290, 1275, 1125, 1015cm$^{-1}$.

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of Formula I. The preferred method of administration is by inhalation into the lung by means of an aerosol liquid or powder for insufflation.

For oral administration, either solid or fluid unit dosage forms can be prepared. For preparing solid compositions such as tablets, the compound of FIG. I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung. For treatment of allergic conditions of the nose, such as rhinitis, compositions adapted for contact with nasal linings are preferred.

Compositions for inhalation are of three basic types: (1) a powder mixture preferably micropulverized with particle size, preferably from about 1 to about 5 microns; (2) an aqueous solution or suspension to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dispersing a compound of Formula I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl, chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"); difluoroethane ("Genetron 142-A") and monochlorotrifluoromethane ("Freon 13").

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.5 to about 50 mg. of compound in a single dose, administered parenterally or by inhalation in the compositions of this invention, are effective for preventing allergy attacks. More specifically, the single dose is from about 2.0 to about 30 mg. of compound. The oral and rectal dose is from about 10 to about 500 mg. in a single dose. More specifically, the single dose is from about 20 to about 250 mg. of compound. The dosage to be administered can be repeated up to four times daily.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, auto-immune diseases, exercise-induced asthma, stress-induced asthma, systemic anaphylaxis, and bird fancier's disease.

EXAMPLE 10

A lot of 10,000 tablets, each containing 50 mg. of 3'-[m-(1-carboxyformamido)benzamido]oxanilic acid, diethyl ester is prepared from the following types and amounts of ingredients:

3'-[m-(1-carboxyformamido)benzamido]oxanilic acid, diethyl ester: 500 Gm.
Dicalcium phosphate: 1,000 Gm.
Methylcellulose, U.S.P. (15 cps): 60 Gm.
Talc: 150 Gm.
Corn starch: 200 Gm.
Magnesium stearate: 10 Gm.

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever or asthma attacks at a dose of one tablet every six hours.

EXAMPLE 11

One thousand tablets, each containing 30 mg. of 3'-[m-(1-carboxyformamido)benzamido]oxanilic acid, diethyl ester are prepared from the following types and amounts of ingredients:

3'-[m-(1-carboxyformamido)benzamido]oxanilic acid, diethyl ester: 30 Gm.
Microcrystalline cellulose NF: 410 Gm.
Starch: 100 Gm.
Magnesium stearate powder: 3 Gm.

The ingredients are screened and blended together and pressed into tablets.

The tablets are useful to protect against food allergy at a dose of one tablet before meals.

EXAMPLE 12

A sterile preparation suitable for intramuscular injection and containing 10 mg. of 3'-[m-(1-carboxyformamido)benzamido]oxanilic acid, diethyl ester in each milliliter is prepared from the following ingredients:

3'-[m-(1-carboxyformamido)benzamido]oxanilic acid, diethyl ester: 10 Gm.
Benzyl benzoate: 200 ml.
Methylparaben: 1.5 Gm.
Propylparaben: 0.5 Gm.
Cottonseed oil q.s.: 1,000 ml.

One milliliter of this sterile preparation is injected for prophylactic treatment of allergic rhinitis.

EXAMPLE 13

Six hundred ml. of an aqueous solution containing 10 mg. of the ditris(hydroxymethyl)aminomethane (THAM) salt of 3'-[m-(1-carboxyformamido)benzamido]oxanilic acid, per ml. is prepared as follows:
THAM salt of 3'-[m-(1-carboxyformamido)benzamido]oxanilic acid: 6 Gm.
Sodium chloride: 5 Gm.
Water for injection q.s.: 600 ml.

The compound of the above formulation and sodium chloride are dispersed in sufficient water to make 600 ml. and sterilized.

The liquid is placed in nebulizers designed to deliver 0.25 ml. per spray.

The liquid is inhaled into the lungs every four to six hours for prevention of asthmatic attacks.

EXAMPLE 14

A powder mixture consisting of 0.2 gram of the THAM salt of 3'-[m-(1-carboxyformamido)benzamido]oxanilic acid, and sufficient lactose to make five grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 15

A powder mixture consisting of 0.2 gram of the sodium salt of 3'-[m-(1-carboxyformamido)benzamido]oxanilic acid, and sufficient lactose to make five grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 16

Twelve grams of an aerosol composition are prepared from the following ingredients:
THAM salt of 3'-[m-(1-carboxyformamido)benzamido]oxanilic acid: 0.750 Gm.
Freon 12: 1.940 Gm.
Freon 114: 2.410 Gm.
Water: 6.300 Gm.
Sorbitan monoleate: 0.600 Gm.

The compound is dispersed in water and added to the Freons. The twelve grams of composition are added to a 13 ml. plastic coated bottle and capped with a metering valve. The metering valve releases 80 mg. of composition in an aerosol. The aerosol is inhaled every four to six hours for prevention of asthmatic attacks.

EXAMPLE 17

After allowing for the differing solubilities of the compounds and the activity of the particular compound as measured, for example, by the in vivo rat passive cutaneous anaphylaxis assay, a suitable quantity of each of the compounds of Table I through Table IV and Examples 1-9 is substituted for the active compound in the compositions and uses of Examples 10-17. Results showing anti-allergy activity are obtained.

EXAMPLE 18

The rat passive cutaneous anaphylaxis assay is run in the following manner:

Female Sprague-Dawley 250 gm. rats are skin-sensitized with rat anti-ovalbumin homocytotropic anti-body that is heat labile and has a passive cutaneous anaphylaxis titer of 1:128. After a 72-hour latency period, the animals are challenged i.v. with 4 mg. ovalbumin (OA)+5 mg. Evans blue dye and the test compound. Thirty minutes later the extra-vascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

It should be noted that in all the compositions and treatment examples of this patent application, the quantity of drug employed refers to the acid equivalent.

When repeated administration is desired, the compounds of this application which have a relatively short duration of activity can be administered in a priming dose-maintenance dose regimen as described in U.S. Ser. No. 382,762 issued as U.S. Pat. No. 3,993,679 at Page 58, line 19 to Page 59, line 9.

Following the procedure of Example 18 of this application, the inhibitory dose$_{50}$ of the THAM salt of 3'-[m-(1-carboxyformamido)benzamido[oxanilic acid, is approximately 0.05 mg./kg. by the intravenous route.

We claim:

1. A method for treating a mammal for an allergic condition selected from the group consisting of asthma, rhinitis, food allergy and urticaria which comprises prophylactically administering to a mammal in need of treatment an anti-asthma, anti-rhinitis, anti-food allergy, or anti-urticaria effective amount of a compound of the formula

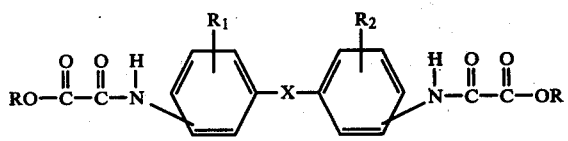

wherein
R is selected from the group consisting of hydrogen, a physiologically acceptable metal or amine cation, alkyl of one to six carbon atoms, inclusive, and

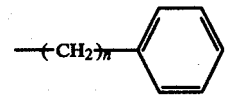

wherein n is 0, 1 or 2;
$R_1$ and $R_2$ are the same or different and are selected from the group consisting of hydrogen, halogen, nitro, cyano and

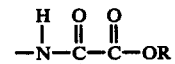

with the proviso that when one or both of $R_1$ and $R_2$ are

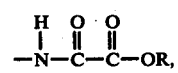

the two

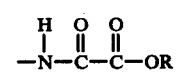

groups on a phenylene ring are not ortho to each other;
X is S, SO, or SO$_2$ in association with a pharmaceutical carrier.

2. A method in accordance with claim 1 wherein
R is selected from the group consisting of hydrogen, a physiologically acceptable metal or amine cation and alkyl of one to six carbon atoms, inclusive;
X is SO$_2$.

3. A method in accordance with claim 2 wherein
R is selected from the group consisting of hydrogen, a physiologically acceptable metal or amine cation and alkyl of one to three carbon atoms, inclusive;
R$_1$ and R$_2$ are the same or different and are selected from the group consisting of hydrogen, halogen, cyano and nitro.

4. A method in accordance with claim 1 wherein the compound is diethyl N,N'-[sulfonylbis-(6-fluoro-m-phenylene)]dioxamate.

5. A method in accordance with claim 1 wherein the compound is N,N'-[sulfonylbis-(6-fluoro-m-phenylene)]dioxamic acid.

6. A pharmaceutical composition which comprises an anti-asthma, anti-rhinitis, anti-food allergy, or anti-urticaria effective amount of a compound of the formula

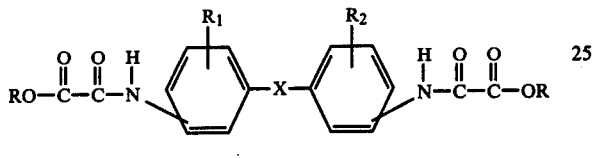

wherein
R is selected from the group consisting of hydrogen and a physiologically acceptable metal or amine cation,
R$_1$ and R$_2$ are the same or different and are selected from the group consisting of hydrogen, halogen, nitro, cyano and

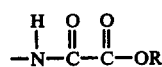

with the proviso that when one or both of R$_1$ and R$_2$ are

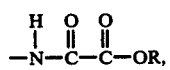

the two

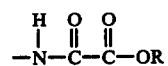

groups on a phenylene ring are not ortho to each other;
X is S, SO, or SO$_2$ in association with a pharmaceutical carrier suitable for inhalation.

7. A pharmaceutical composition which comprises an anti-asthma, anti-rhinitis, anti-food allergy or anti-urticaria effective amount of a compound of the formula

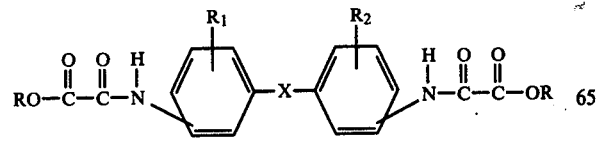

wherein

R is selected from the group consisting of hydrogen and a physiologically acceptable metal or amine cation;
R$_1$ and R$_2$ are the same or different and are selected from the group consisting of hydrogen, halogen, nitro, cyano and

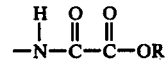

with the proviso that when one or both of R$_1$ and R$_2$ are

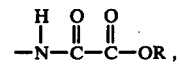

the two

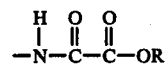

groups on a phenylene ring are not ortho to each other;
X is S, SO, or SO$_2$ in association with a pharmaceutical carrier.

8. A pharmaceutical composition in accordance with claim 7 wherein
R$_1$ and R$_2$ are the same or different and are selected from the group consisting of hydrogen, halogen, cyano and nitro; and
X is S.

9. A pharmaceutical composition which comprises as the sole active ingredient an anti-asthma, anti-rhinitis, anti-food allergy, or anti-urticaria effective amount of a compound of the formula

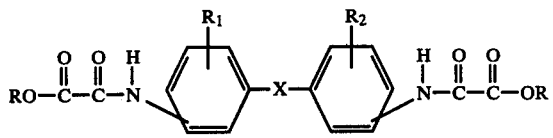

wherein
R is selected from the group consisting of hydrogen, a physiologically acceptable metal or amine cation, alkyl of one to six carbon atoms, inclusive, and

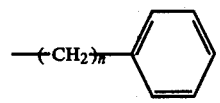

wherein n is 0, 1 or 2;
R$_1$ and R$_2$ are the same or different and are selected from the group consisting of hydrogen, halogen, nitro, cyano and

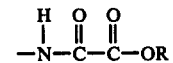

with the proviso that when one or both of R$_1$ and R$_2$ are

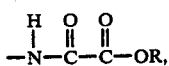
the two
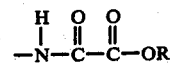
groups on a phenylene ring are not ortho to each other;
S, SO is $SO_2$ in association with a pharmaceutical carrier and in the dosage form of capsule, tablet, or aerosol for inhalation.
* * * * *

UNITED STATES PATENT OFFICE
CERTIFICATE OF CORRECTION

Patent No. 4,159,341         Dated    June 26, 1979

Inventor(s)   Charles M. Hall, John B. Wright

It is certified that error appears in the above-identified patent and that said Letters Patent are hereby corrected as shown below:

Column 10, line 47:  "$C_{20}H_{20}N_2O_3$" should read -- $C_{20}H_{20}N_2O_6$ --
Column 20, line 8 :  "S,SO is $SO_2$" should read -- X is —$(CH_2)_{\overline{m}}$— wherein m is S, SO or $SO_2$ --

Signed and Sealed this

Sixteenth Day of October 1979

[SEAL]

Attest:

RUTH C. MASON
Attesting Officer

LUTRELLE F. PARKER
Acting Commissioner of Patents and Trademarks